United States Patent [19]

Sawicki et al.

[11] Patent Number: 5,070,058

[45] Date of Patent: Dec. 3, 1991

[54] METHOD FOR MAKING A CATALYST COMPOSITION USED IN THE PRODUCTION OF LOWER ALIPHATIC ALCOHOLS

[75] Inventors: Robert A. Sawicki, Stormville; Jeffrey B. Harrison, Fishkill, both of N.Y.

[73] Assignee: Texaco, Inc., White Plains, N.Y.

[21] Appl. No.: 468,325

[22] Filed: Jan. 22, 1990

[51] Int. Cl.$^5$ .................. B01J 23/02; B01J 23/06; B01J 23/28; B01J 23/72

[52] U.S. Cl. .................. 502/206; 502/244; 502/307

[58] Field of Search ............... 502/307, 321, 343, 345, 502/206, 244; 518/713

[56] References Cited

U.S. PATENT DOCUMENTS

| | | | |
|---|---|---|---|
| 2,857,442 | 10/1958 | Hay | 502/317 X |
| 3,363,023 | 1/1968 | Mooi et al. | 502/306 X |
| 4,513,100 | 4/1985 | Fattore et al. | 502/307 X |
| 4,657,887 | 4/1987 | Hardman et al. | 502/343 X |

FOREIGN PATENT DOCUMENTS 60-197633  10/1985  Japan .................... 502/307

*Primary Examiner*—W. J. Shine
*Attorney, Agent, or Firm*—Robert A. Kulason; James J. O'Loughlin; Dominick G. Vicari

[57] ABSTRACT

A method for preparing a catalyst composition is disclosed. In particular, a support is vacuum impregnated with at least one catalytically active element and, thereafter, the vacuum impregnated support is calcined to provide the catalyst composition. Preferably, the vacuum impregnation of the support is performed in a two-step sequence by (a) vacuum impregnating said support with said at least one element and, thereafter, calcining said support, and (b) vacuum impregnating said support with at least one other element.

The catalyst composition prepared by the prescribed method is preferably used in a process for producing a mixture of lower aliphatic alcohols.

20 Claims, No Drawings

METHOD FOR MAKING A CATALYST COMPOSITION USED IN THE PRODUCTION OF LOWER ALIPHATIC ALCOHOLS

BACKGROUND OF THE INVENTION

1. Field of the Invention

This invention relates to a method for preparing a catalyst composition which is used to produce a mixture of lower aliphatic alcohols. The mixture of lower aliphatic alcohols so produced is characterized by containing a substantial proportion of alcohols having from 2 to 6 carbon atoms.

2. Description of Background Art

Lower aliphatic alcohols have been proposed as fuel extenders or as replacements for gasoline for fueling internal combustion engines. Their value as gasoline additives for octane enhancement has also been recognized. Additionally, lower aliphatic alcohols exhibit great commercial potential as commodity chemicals and are excellent cosolvents for methanol in an alcohol/gasoline blend. Certain mixtures of lower aliphatic alcohols have the EPA approval for use and are currently being marketed in the United States. The lower aliphatic alcohols can be produced from domestically available non-petroleum sources and their use in fuels would serve to lessen the dependence of the nation on imported petroleum and petroleum products.

Hydrogen and carbon monoxide, or a synthesis gas mixture of hydrogen and carbon monoxide, can be reacted to form lower aliphatic alcohols. The synthesis gas feed stream can be produced from non-petroleum sources, such as coal, biomass or other hydrocarbonaceous materials. The synthesis gas mixture itself is produced in a partial oxidation reaction of the hydrocarbonaceous materials in commercially available processes, such as coal gasification.

Numerous catalysts and catalytic processes have been studied in attempts to provide a viable process for the production of aliphatic alcohols from synthesis gas or from a mixture of hydrogen and carbon monoxide. Heretofore, the emphasis has been primarily directed to the production of methanol. In contrast, the present invention is directed to a process for making a catalyst composition which is used for producing an alcohol mixture containing a substantial amount of aliphatic alcohols having from 2 to 6 carbon atoms.

Catalysts which are selective for alcohol synthesis, especially methanol or a mixture of lower aliphatic alcohols, are typically prepared via a precipitation or coprecipitation technique. As reported in Nunan, J. et al., "Promotion of Methanol Synthesis over Cu/ZnO Catalysts by Doping with Caesium", J. CHEM. SOC., CHEM. COMMUN., p. 193 (1986), in most instances the nitrate salts are dissolved in water and are precipitated by the addition of a carbonate or hydroxide base. As a result, a hydroxy carbonate or hydrous oxide precursor is formed which is thereafter calcined to the corresponding metal oxide. U.S. Pat. Nos. 4,507,403 and 4,522,938 each describe a method for producing a methanol catalyst via coprecipitation. Similarly, U.S. Pat. Nos. 4,440,668 and 4,562,174 describe catalysts which are also prepared by a coprecipitation technique.

One of the shortcomings associated with the known processes of preparing a catalyst composition by precipitation or coprecipitation includes the difficulty of reproducing the technique so that substantially similar products can be provided. Also, the cumbersome equipment used in preparing the catalyst composition and the lack of control one has over the metal concentrations and the physical relationship of the various metals with respect to each other are other difficulties which have heretofore been encountered.

A process for producing lower aliphatic alcohols from a mixture of carbon monoxide and hydrogen is described in U.S. Pat. No. 4,096,164. The process includes reacting hydrogen and carbon monoxide in the presence of a solid catalyst comprising rhodium with molybdenum or tungsten to produce two carbon atom oxygenated hydrocarbons in which ethanol is the major component. This disclosure is incorporated herein by reference.

U.S. Pat. No. 4,380,589 describes a Fischer-Tropsch process for producing hydrocarbons with improved selectivity to $C_2$–$C_4$ olefins by contacting hydrogen and carbon monoxide with a catalyst including molybdenum, a promoter comprising an alkali or alkaline earth metal and a binder comprising an iron-containing calcium aluminate cement.

U.S. Pat. No. 4,607,055 describes a process for producing lower aliphatic alcohols from a mixture of carbon monoxide and hydrogen in the presence of a catalyst comprising molybdenum; a metal from the group consisting of cobalt, iron and nickel; and silver. The catalyst is modified by the addition of a promoter from the class consisting of potassium, cesium and rubidium. This disclosure is incorporated herein by reference.

U.S. Pat. No. 4,661,525 describes a process for producing lower aliphatic alcohols from a mixture of carbon monoxide and hydrogen in the presence of a catalyst comprising molybdenum and a metal selected from the group consisting of cobalt, iron and nickel which has been promoted by an alkali metal selected from the group consisting of potassum, cesium and rubidium. This disclosure is incorporated herein by reference.

European Patent Application No. 119609 describes a process for producing alcohols from synthesis gas using a catalyst which includes molybdenum with tungsten, rhenium and an alkali metal. This disclosure is incorporated herein by reference. European Patent No. 79132 describes a similar process in which the catalyst contains rhenium, molybdenum and potassium.

Co-assigned application Ser. No. 939,392 filed on Dec. 12, 1986, now abandoned, is directed to a process for producing lower aliphatic alcohols from a mixture of carbon monoxide and hydrogen in the presence of a catalyst comprising rhodium, molybdenum and an alkali metal. This disclosure is incorporated herein by reference.

Previous catalytic processes have been notably effective for converting carbon monoxide and hydrogen feedstocks into hydrocarbons or methanol, but none have been particularly effective for providing a substantial yield of a lower aliphatic alcohol mixture having from 2 to 6 carbon atoms along with the coproduced methanol. It is the present method for preparing the catalyst which produces a catalyst that exhibits favorable productivity and selectivity for the aforestated mixture of lower aliphatic alcohols and, further, which overcomes those shortcomings identified above.

SUMMARY OF THE INVENTION

Accordingly, in a broad aspect, the present invention relates to a method for preparing a catalyst composition which comprises vacuum impregnating a support with at least one catalytically active element and calcining said vacuum impregnated support to provide said catalyst composition. Preferably, the vacuum impregnation of the support is performed in a two-step sequence by (a) vacuum impregnating said support with said at least one element and, thereafter, calcining said support, and (b) vacuum impregnating said support with at least one other element.

The catalyst composition prepared by the prescribed method is preferably used in a process for producing a mixture of lower aliphatic alcohols. When used in this capacity, the elements comprising the catalyst composition can include copper, zinc, molybdenum and/or an alkali metal or metals, such as cesium.

DETAILED EMBODIMENTS OF THE INVENTION

In general, an efficient catalyst which is selective for the production of alcohols other than methanol requires several active sites to support the reaction scheme. Included among these sites are a carbon monoxide adsorption site, a dissociation site, a hydrogenation site and a chain growth site. The first three of the aforestated sites are available in a standard copper-zinc methanol catalyst. In accordance with the present invention, the standard copper-zinc methanol catalyst is modified with a molybdenum promoter to impart the chain growth site needed for the production of alcohols other than methanol. Moreover, the present method of preparing the catalyst composition, as described hereinbelow, is significant in achieving the increased catalytic activity exhibited by the resulting catalyst composition.

The present method for preparing the catalyst composition includes impregnating a carrier or support with the catalyst components via vacuum impregnation. In connection with the subject invention, the term "vacuum impregnation" or a term of similar import, such as "vacuum coimpregnation" is intended to mean dissolving a salt or salts of the element or elements to be impregnated in an appropriate solvent known to those skilled in the art, insuring complete dissolution, adding the support to this solution, and removing the solvent by slow evaporation at less than atmospheric pressure. Most preferably, the catalyst components are impregnated by a slow vacuum impregnation procedure. The term "slow" shall be construed to mean at a rate which approximates a 50% solvent removal per hour. While all of the catalyst components may be vacuum impregnated at the same time, in a preferred embodiment, the catalyst components are vacuum impregnated to the support in a sequence which constitutes two steps or, simply, a double impregnation. Specifically, the carrier or support is first vacuum coimpregnated with a source of copper and zinc, generally in the form of a water soluble salt. The impregnated carrier is thereafter subjected to an intermediate step of drying and calcining according to known procedures. Where the water soluble salt employed is a nitrate, the impregnated carrier is preferably calcined in a nitrogen atmosphere to decompose the nitrate salts to metal oxides.

The carrier, now impregnated with copper and zinc, is vacuum impregnated once again; this time, however, with a source of molybdenum, also generally in the form of a water soluble salt. The twice impregnated carrier is again dried and calcined in accordance with the procedure described above. For promoting the production of a mixture of lower aliphatic alcohols, an alkali metal or mixture of alkali metals are added to the catalyst composition in the first or second step by the vacuum impregnation method or, alternatively, by pore volume filling (incipient wetness) impregnation. Preferably, the alkali metal employed is selected from cesium, potassium, sodium and rubidium or a mixture of same, with cesium being the most preferred alkali metal. The resulting catalyst is then subjected to reduction with hydrogen gas generally by heating the promoted catalyst at a temperature between about 300° C. to about 500° C. for an extended period; usually about 2 to about 8 hours.

Alternatively, the two vacuum impregnation steps of the sequence described above can be performed in reverse order. That is, the molybdenum can be vacuum impregnated first, impregnated carrier can thereafter be vacuum impregnated with copper and zinc, followed again by calcining and drying, the addition of the alkali promoter and reduction with hydrogen gas. Again, the alkali metal or metals can be vacuum impregnated in either step or, alternatively, can be added via the incipient wetness technique.

The carrier or support generally comprises a relatively refractory, porous, adsorptive and high surface area material. Conventional carriers or supports, such as alumina, silica, titania, magnesia, silica-alumina and boron phosphates, to name a few, are suitable support materials for preparing the catalyst via this method. Other conventional carriers or supports are to be considered within the scope of this invention. The disclosure in U.S. Pat. No. 4,098,683 is illustrative and is incorporated herein by reference.

A mixture of carbon monoxide and hydrogen, for example, a synthesis gas mixture of said reactants, is reacted over the present catalyst which, again, includes copper, zinc, a molybdenum promoter and an alkali promoter. The catalyst composition comprises from about 1 to about 20 weight percent copper, from about 1 to about 20 weight percent zinc, from about 0.1 to about 10 weight percent molybdenum and from about 1 to about 25 weight percent of the alkali metal or metals. A preferred catalyst composition comprises from about 2 to about 6 weight percent copper, from about 5 to about 10 weight percent zinc, from about 2 to about 8 weight percent molybdenum and from about 5 to about 15 weight percent alkali metal or metals.

The catalyst should have a surface area of at least about 50 m$^2$/gm (square meters per gram of catalyst) or more. A more preferred catalyst will have a surface area of from about 100 m$^2$/gm to about 400 m$^2$/gm and the most preferred will have a surface area of from about 200 m$^2$/gm to about 300 m$^2$/gm.

The carbon monoxide and hydrogen, or a mixture of same, employed to form the lower aliphatic alcohols in this method can be provided from any available source. One particularly useful source is synthesis gas which, for instance, is produced in the gasification of hydrocarbonaceous materials, such as oil, coals and biomass. An effective gasification process is described in U.S. Pat. No. 3,544,291 where a hydrocarbonaceous fuel is partially oxidized with a free oxygen-containing gas in a gas generator. In general, the mole ratio of hydrogen to carbon monoxide employed in the process for producing the lower aliphatic alcohol mixture should range from about 0.1 to about 50 moles of hydrogen per mole of carbon monoxide, with the preferred ratio being from about 0.5 to about 5 moles of hydrogen per mole of carbon monoxide.

The reaction conditions for effecting the conversion of the carbon monoxide-hydrogen feed into lower aliphatic alcohols employing the catalyst produced by the process of the present invention include a reaction temperature ranging from about 200° C. to about 400° C., with the preferred temperature ranging from about 250° C. to about 350° C.

Effective hydrogenation of carbon monoxide is accomplished at elevated pressures. An effective pressure range for this process is from about 200 to about 3500 psig. A preferred pressure range is from about 500 to about 2000 psig.

The space velocity employed to effect the conversion of produce the aliphatic alcohols is a significant feature of this process. In general, the space velocity, that is, the volume of gas passed through a given volume of catalyst per hour expressed as GHSV (hr$^{-1}$), must be at least about 500. A preferred range is from about 1000 to about 50,000. A highly effective process is realized when the space velocity employed ranges from about 5000 to about 20,000.

Advantageously, when the present catalyst composition is prepared in accordance with the method described above, it exhibits favorable characteristics of activity, productivity and selectivity for lower aliphatic alcohols, inasmuch as it permits deposition of the metal salts in a highly dispersed mode. In particular, at an atomic level the individual atoms or ions are randomly distributed across the surface of the support material. On a larger scale, the catalytic metals are distributed on the surface of the support as a uniform single layer. This arrangement results in the maximum number of catalytic sites and prevents the segregation or sintering of the metals into separate solid phases.

Additionally, by preparing the catalyst in accordance with the method of this invention, one skilled in the art is permitted to vary the sequence of addition of each component, combine one or more sequences into single steps, and vary the percentage of each component.

Examples I–IX(B) are provided to further describe preferred embodiments of the present invention and should not be construed as limiting it in any way.

The catalysts produced in Examples I–IX(B) were prepared by slow vacuum impregnation of the components, in the form of the corresponding water soluble nitrate or ammonium oxide salts, onto the inert support identified in each of the examples and in Table I. Where the component was impregnated in the form of the corresponding water soluble nitrate or ammonium oxide salt, calcination was conducted in a nitrogen atmosphere to decompose the nitrate salts or ammonium oxide to metal oxides. In all instances, the resulting product was characterized by elemental analysis.

EXAMPLE I

A catalyst was prepared by adding 250 ml water, 25 g (0.084 moles) zinc nitrate hexahydrate, 10.5 g (0.043 moles) cupric nitrate trihydrate and 50 g alumina (Norton) into a 500 ml single neck flask. After stripping the solvent slowly on a rotary evaporator under vacuum at 65° C., the light blue solid was dried overnight in a vacuum oven at 110° C. The catalyst (76.4 g) was calcined under nitrogen at 375° C. for four hours to yield a green powder which was analyzed for Cu (4.62 wt. percent) and Zn (8.92 wt. percent).

EXAMPLE II

A catalyst was prepared in accordance with Example I except that 2.5 g (0.009 moles) cobalt nitrate hexahydrate was also added to the flask. The resulting product was stripped, dried and calcined as in Example I. The product was then analyzed for Cu (4.76 wt. percent), Zn (9.07 wt. percent) and Co (0.82 wt. percent).

EXAMPLE III

A catalyst was prepared in accordance with Example I except that 4.0 g (0.003 moles) of ammonium heptamolybdate was also added to the flask. The resulting product was stripped, dried and calcined as in Example I. The product was then analyzed for Cu (4.56 wt. percent), Zn (8.58 wt. percent) and Mo (3.50 wt. percent).

EXAMPLE IV

A catalyst was prepared by adding 250 ml water, 3.7 g ammonium heptamolybdate (0.003 moles) and 50 g of the product resulting from Example I into a 500 ml single neck flask. The resulting product was stripped, dried and calcined as in Example I. The product was analyzed for Cu (4.18 wt. percent), Zn (7.94 wt. percent) and Mo (3.76 wt. percent).

EXAMPLE V

A catalyst was prepared in accordance with Example IV, except that 5.6 g (0.0045 moles) ammonium heptamolybdate were employed. The resulting product was stripped, dried and calcined as in Example I. The product was analyzed for Cu (4.02 wt. percent), Zn (7.80 wt. percent) and Mo (5.31 wt. percent).

EXAMPLE VI

A catalyst was prepared in accordance with Example IV, except that 7.4 g (0.006 moles) ammonium heptamolybdate was employed. The resulting product was stripped, dried and calcined as in Example I. The produced was analyzed for Cu (4.16 wt. percent), Zn (7.78 wt. percent) and Mo (6.85 wt. percent).

EXAMPLE VII

A catalyst was prepared by adding 250 ml water, 0.6 g (0.0025 moles) cobalt nitrate hexahydrate and 50 g of the product resulting from Example IV into a 500 ml single neck flask. The resulting product was stripped, dried and calcined as in Example I. The product was analyzed for Cu (4.16 wt. percent), Zn (8.05 wt. percent), Mo (3.66 wt. percent) and Co (0.21 wt. percent).

EXAMPLE VIII

A catalyst was prepared by adding 250 ml water, 3.7 g (0.003 moles) ammonium heptamolybdate and 50 g alumina into a 500 ml single neck flask. The resulting product was stripped, dried and calcined as in Example I to produce a white powder containing 3.96 wt. percent Mo. A 20 g portion of this powder was added to a flask containing 100 ml water, 10 g (0.035 moles) zinc nitrate hexahydrate and 4 g (0.016 moles) cupric nitrate trihydrate. The mixture was stripped, dried and calcined as in Example I and the product was analyzed for Cu (4.56 wt. percent), Zn (8.58 wt. percent) and Mo (3.50 wt. percent).

EXAMPLE IX(A)

A catalyst was prepared by adding 20 ml water, 5 g (0.017 moles) zinc nitrate hexahydrate, 2.1 g (0.009 moles) cupric nitrite trihydrate and 10 g titania (Degussa, 20-80 mesh) into a 500 ml single neck flask. The resulting product was stripped, dried and calcined as in Example I. The product was then analyzed for Cu (4.30 wt. percent) and Zn (9.13 wt. percent).

EXAMPLE IX(B)

A catalyst was prepared by adding 25 ml water, 0.4 g (0.0003 moles) ammonium heptamolybdate and 5 g of the product produced in Example IX(A) to a 500 ml single neck flask. The resulting product was stripped, dried and calcined as in Example I. The product was then analyzed for Cu (4.65 wt. percent), Zn (8.76 wt. percent) and Mo (3.77 wt. percent).

The catalysts produced in Examples I–IX(B) were screened for activity using a micro fixed-bed reactor under the following standard reaction conditions: catalyst weight (1.00 gram); temperature (260° C.-320° C.); pressure (1400 psig); gas hourly space velocity (GHSV) (10,800 hr$^{-1}$); and H$_2$/CO ratio (2:1). Prior to evaluation, a cesium promoter was added to the catalyst via the incipient wetness technique. Typically, 10% cesium by weight of the salt was added. The catalyst was reduced in hydrogen at 400° C. for 4 hours at 1500 psi and 10,000 hr$^{-1}$ GHSV. The products, both gas and liquid, were quantified by gas chromatography; the results are provided hereinbelow in Table II.

The catalysts produced in Examples IV–VII were screened for activity in a larger unit under the following reaction conditions: catalyst volume (30 cc); temperature (290° C.-310° C.); pressure (1500 psig); GHSV (10,000 hr$^{-1}$); and H$_2$/CO ratio (2:1). The larger unit was a reactor system which consisted of four fixed bed reactors, each ½ inch in diameter with a maximum catalyst volume of 40 cc. All four reactors were immersed and heated in a molten salt bath to insure good heat transfer. Prior to evaluation a cesium promoter was added to the catalyst via the incipient wetness technique. The catalysts were reduced in hydrogen prior to evaluation. The products formed in the reaction were analyzed and quantified by gas chromatography. The results appear below in Table III.

As a matter of convenience, Table I delineates the components present in the catalysts prepared in Examples I to VIII and IX(B) and further sets forth the respective weight percentages of each component.

TABLE I

| Example | Support | Metals Concentration (wt. %) | | | |
| --- | --- | --- | --- | --- | --- |
| | | % Cu | % Zn | % Mo | % Co |
| I | Al$_2$O$_3$ | 4.62 | 8.92 | 0 | 0 |
| II | Al$_2$O$_3$ | 4.76 | 9.07 | 0 | 0.82 |
| III | Al$_2$O$_3$ | 4.56 | 8.58 | 3.50 | 0 |
| IV | Al$_2$O$_3$ | 4.18 | 7.94 | 3.76 | 0 |
| V | Al$_2$O$_3$ | 4.02 | 7.80 | 5.31 | 0 |
| VI | Al$_2$O$_3$ | 4.16 | 7.78 | 6.85 | 0 |
| VII | Al$_2$O$_3$ | 4.16 | 8.05 | 3.66 | 0.21 |
| VIII | Al$_2$O$_3$ | 4.56 | 8.58 | 3.50 | 0 |
| IX(B) | TiO$_2$ | 4.65 | 8.76 | 3.77 | 0 |

The data provided in Tables II and III may be interpreted pursuant to the following representations:
Rxn Temp.=reaction temperature (°C.)
Productivity=alcohol productivity (g/g/-hr)
Selectivity=alcohol sensitivity (CO$_2$ free)
HA=weight percent higher alcohols (C$_2$-C$_6$) in product
C$_{2+}$OH/C$_1$OH=ratio of higher alcohols (C$_2$-C$_6$) to methanol on a weight basis

TABLE II

| Catalyst | Rxn Temp. | Productivity | Selectivity | HA |
| --- | --- | --- | --- | --- |
| Example I | 287 | .313 | 97 | 1 |
| | 304 | .417 | 97 | 1 |
| Example II | 287 | .054 | 90 | 1 |
| | 302 | .067 | 90 | 2 |
| Example III | 303 | .039 | 83 | 8 |
| | 314 | .057 | 81 | 12 |
| Example IV | 290 | .061 | 76 | 25 |
| | 308 | .112 | 78 | 28 |
| | 321 | .157 | 68 | 31 |
| Example V | 294 | .074 | 72 | 27 |
| | 305 | .124 | 72 | 29 |
| Example VI | 294 | .070 | 69 | 29 |
| | 304 | .124 | 72 | 29 |
| Example VII | 294 | .063 | 76 | 22 |
| | 303 | .079 | 74 | 24 |
| Example VIII | 296 | .066 | 77 | 28 |
| | 313 | .097 | 70 | 38 |
| Example IX | 291 | .048 | 81 | 29 |
| | 307 | .080 | 77 | 32 |

TABLE III

| Catalyst | Rxn Temp. | Productivity | Selectivity | C$_{2+}$OH/C$_1$OH |
| --- | --- | --- | --- | --- |
| Example IV | 296 | 0.136 | 74.3 | 0.566 |
| Example V | 296 | 0.113 | 71.3 | 0.699 |
| Example VI | 297 | 0.124 | 67.2 | 0.756 |
| Example VII | 294 | 0.130 | 68.1 | 0.623 |

As these data demonstrate, the catalyst of Examples I–VIII and IX(B), which employ molybdenum as the primary catalytic metal and which were prepared in accordance with the sequential impregnation method of the present invention, exhibit excellent selectivity and productivity to higher alcohols.

What is claimed is:

1. A method for preparing a catalyst composition which comprises (a) vacuum impregnating a support with at least one catalytically active element and, thereafter, calcining said vacuum impregnated support and (b) vacuum impregnating said support with at least one other element to provide said catalyst composition.

2. The method of claim 1 wherein said support is vacuum impregnated by dissolving a salt of said at least one catalytically active element, and said at least one other element in a solvent to provide a solution of said at least one catalytically active element, and said at least one other element, adding said support to said solution and removing said solvent from said solution by evaporation at less than atmospheric pressure and at a rate of about 50 percent solvent removal per hour.

3. The method of claim 1 which further comprises reducing said catalyst composition.

4. The method of claim 3 wherein said catalyst composition is reduced with hydrogen gas at a temperature of about 300° C. to about 500° C. for about 2 to about 8 hours.

5. A method for preparing a catalyst composition used in a process for producing a mixture of lower aliphatic alcohols, said method comprising (a) vacuum impregnating a support with at least one element which is catalytically active for producing said mixture and, thereafter, calcining said vacuum impregnated support and (b) vacuum impregnating said support with at least one other element to provide said catalyst composition.

6. The method of claim 5 wherein said support is vacuum impregnated by dissolving a salt of said at least one catalytically active element, and said at least one other element in a solvent to provide a solution of said at least one catalytically active element, and said at least one other element, adding said support to said solution and removing said solvent from said solution by evaporation at less than atmospheric pressure and at a rate of about 50 percent solvent removal per hour.

7. The method of claim 5 which further comprises reducing said catalyst composition.

8. The method of claim 7 wherein said catalyst composition is reduced with hydrogen gas at a temperature of about 300° C. to about 500° C. for about 2 to about 8 hours.

9. The method of claim 5 wherein said at least one element and said at least one other element include copper, zinc, molybdenum and an alkali metal or mixture of alkali metals.

10. The method of claim 9 wherein said alkali metal or mixture of alkali metals is selected from the group consisting of cesium, potassium, sodium and rubidium.

11. The method of claim 5 wherein said support is selected from the group consisting of alumina, silica, titania, magnesia, silica-alumina and boron phosphate.

12. The method of claim 9 wherein said catalyst composition includes from about 1 to about 20 weight percent of copper; from about 1 to about 20 weight percent of zinc; from about 0.1 to about 10 weight percent of molybdenum, and from about 1 to about 25 weight percent of said alkali metal or mixture of alkali metals.

13. A method for preparing a catalyst composition used in a process for producing a mixture of lower aliphatic alcohols, said method comprising vacuum impregnating a support with copper and zinc, calcining said vacuum impregnated support, vacuum impregnating said support with molybdenum and calcining the twice vacuum impregnated support to produce said catalyst composition.

14. The method of claim 13 which further comprises adding an alkali metal or mixture of alkali metals to said catalyst composition.

15. The method of claim 13 wherein said support is vacuum impregnated with copper and zinc, and molybdenum, by dissolving a salt of said copper and zinc, and molybdenum, in a solvent to provide a solution of said copper and zinc, and molybdenum, adding said support to said solution and removing said solvent from said solution by evaporation at less than atmospheric pressure and at a rage of about 50 percent solvent removal per hour.

16. The method of claim 13 which further comprises reducing said catalyst composition.

17. The method of claim 16 wherein said catalyst composition is reduced with hydrogen gas at a temperature of about 300° C. to about 500° C. for about 2 to about 8 hours.

18. The method of claim 14 wherein said alkali metal or mixture of alkali metals is selected from the group consisting of cesium, potassium, sodium and rubidium.

19. The method of claim 13 wherein said support is selected from the group consisting of alumina, silica, titania, magnesia, silica-alumina, and boron phosphate.

20. The method of claim 13 wherein said catalyst composition includes from about 1 to about 20 weight percent of copper; from about 1 to about 20 weight percent of zinc; from about 0.1 to about 10 weight percent of molybdenum, and from about 1 to about 25 weight percent of said alkali metal or mixture of alkali metals.

* * * * *

UNITED STATES PATENT AND TRADEMARK OFFICE
CERTIFICATE OF CORRECTION

PATENT NO. : 5,070,058
DATED : Dec. 3, 1991
INVENTOR(S) : Robert A. Sawicki, et al.

It is certified that error appears in the above-identified patent and that said Letters Patent is hereby corrected as shown below:

Col. 10, line 13, "rage" should read "rate".

Signed and Sealed this

Twenty-fifth Day of May, 1993

*Attest:*

MICHAEL K. KIRK

*Attesting Officer*  *Acting Commissioner of Patents and Trademarks*